United States Patent [19]
Peters

[11] Patent Number: 5,762,624
[45] Date of Patent: Jun. 9, 1998

[54] VENOUS CANNULA

[75] Inventor: William S. Peters, Tamarama, Australia

[73] Assignee: Heartport, Inc., Redwood City, Calif.

[21] Appl. No.: 879,545

[22] Filed: Jun. 20, 1997

Related U.S. Application Data

[60] Continuation of Ser. No. 614,634, Mar. 13, 1996, abandoned, which is a division of Ser. No. 427,384, Apr. 24, 1995, Pat. No. 5,725,496, which is a division of Ser. No. 159,815, Nov. 30, 1993, Pat. No. 5,433,700.

[30] Foreign Application Priority Data

Dec. 3, 1992 [AU] Australia ............... PL617U

[51] Int. Cl.$^6$ ............... A61M 37/00
[52] U.S. Cl. ............... 604/4; 604/101; 606/194
[58] Field of Search ............... 604/4, 43, 49, 604/96, 101, 102, 280; 606/194, 196

[56] References Cited

U.S. PATENT DOCUMENTS

| | | |
|---|---|---|
| 3,769,960 | 11/1973 | Robinson . |
| 3,833,003 | 9/1974 | Taricco . |
| 4,173,981 | 11/1979 | Mortensen et al. . |
| 4,248,224 | 2/1981 | Jones . |
| 4,276,874 | 7/1981 | Wolvek et al. . |
| 4,527,549 | 7/1985 | Gabbay . |
| 4,531,936 | 7/1985 | Gordon . |
| 4,540,399 | 9/1985 | Litzie et al. . |
| 4,592,340 | 6/1986 | Boyles . |
| 4,601,713 | 7/1986 | Fuqua . |

(List continued on next page.)

FOREIGN PATENT DOCUMENTS

| | | |
|---|---|---|
| 0218275 | 4/1987 | European Pat. Off. . |
| WO 91/08791 | 6/1991 | WIPO . |
| 92/17118 | 10/1992 | WIPO . |

OTHER PUBLICATIONS

Cosgrove, D.M. "Management of the Calcified Aorta: An Alternative Method of Occlusion" *Ann Thorac Surg.* 36:718–719 (1983).

J.H. Foster and J.B. Threlkel "Proximal Control of Aorta with a Balloon Catheter" *Surg, Gynecology & Obstetrics* pp. 693–694 (1971).

H.G. Erath, Jr. and William S. Stoney, Jr. "Balloon Catheter Occlusion of the Ascending Aorta" *Ann Thorac Surg.* 35:560–561 (1983).

Buckberg, G.D., "Strategies and Logic of Cardiplegic Delivery to prevent, Avoid, and Reverse Ischemic and Reperfusion Damage" J Thorac Cardio Vasc Surg. 1987, 93:127–129.

Yamaguchi, A., "A Case of a Reoperation Using a Balloon Catheter with Blocked Pars Ascendes Aortae" Kyobu Geka, Oct. 1991, 42(11):961–964.

Rossi, F., "Long–Term Cardiopulmonary Bypass by Peripheral Cannulation in a Model of Total Heart Failure" J Thorac Cardio Vasc Surg, 1990, 100:914–921.

Sabiston, D.C., Textbook of Surgery, 10th Ed., 1972, pp. 2021–2023, 2114–2121.

(List continued on next page.)

*Primary Examiner*—Michael Buiz
*Assistant Examiner*—A. T. Nguyen
*Attorney, Agent, or Firm*—Jeffry J. Grainger; Jens E. Hoekendijk; Michael J. Lynch

[57] ABSTRACT

A process for inducing cardioplegic arrest of a heart in situ in a patient's body, comprising maintaining the patient's systemic circulation by peripheral cardiopulmonary by-pass, occluding the ascending aorta through a percutaneously placed arterial balloon catheter, venting the left side of the heart, and introducing a cardioplegic agent into the coronary circulation. This procedure readies the heart for a variety of surgical procedures that can be performed percutaneously through lumina in the catheter. An aortic catheter for use in the process is also described.

6 Claims, 6 Drawing Sheets

U.S. PATENT DOCUMENTS

| | | |
|---|---|---|
| 4,655,746 | 4/1987 | Daniels et al. . |
| 4,664,125 | 5/1987 | Pinto . |
| 4,680,029 | 7/1987 | Ranford et al. . |
| 4,697,574 | 10/1987 | Karcher et al. . |
| 4,705,507 | 11/1987 | Boyles . |
| 4,741,328 | 5/1988 | Gabbay . |
| 4,785,795 | 11/1988 | Singh . |
| 4,804,365 | 2/1989 | Litzie et al. . |
| 4,877,035 | 10/1989 | Bogen et al. . |
| 4,889,137 | 12/1989 | Kolobow . |
| 4,902,272 | 2/1990 | Milder et al. . |
| 4,902,273 | 2/1990 | Choy et al. . |
| 4,943,275 | 7/1990 | Stricker . |
| 4,990,139 | 2/1991 | Jang . |
| 5,011,469 | 4/1991 | Buckberg et al. . |
| 5,059,178 | 10/1991 | Ya ............................................ 604/101 |
| 5,116,305 | 5/1992 | Milder et al. . |
| 5,163,906 | 11/1992 | Ahmadi .................................. 604/101 |
| 5,167,628 | 12/1992 | Boyles . |
| 5,171,232 | 12/1992 | Castillo et al. . |
| 5,176,619 | 1/1993 | Segalowitz . |
| 5,186,713 | 2/1993 | Raible . |
| 5,195,942 | 3/1993 | Weil et al. . |
| 5,209,723 | 5/1993 | Twardowski et al. ..................... 604/43 |
| 5,219,326 | 6/1993 | Hattler . |
| 5,254,097 | 10/1993 | Schock et al. . |
| 5,306,249 | 4/1994 | Don Michel ............................. 604/101 |
| 5,308,320 | 5/1994 | Safar . |
| 5,312,344 | 5/1994 | Grinfeld et al. . |
| 5,451,207 | 9/1995 | Yock . |
| 5,460,610 | 10/1995 | Don Michael ........................... 604/101 |
| 5,478,309 | 12/1995 | Sweezer et al. ....................... 604/96 X |
| 5,499,996 | 3/1996 | Hill . |
| 5,562,606 | 10/1996 | Huybregts . |

OTHER PUBLICATIONS

Uchida et al., "Percutaneous Cardiomyotomy and Valvulotomy with Angioscopic Guidance" American Heart Journal, 1991, 121(4, part 1):1221–1224.

Uchida et al., "Percutaneous Fiberoptic Angioscopy of the Cardiac Valves" American Heart Journal, 1991, 121 (6, part 1):1791–98.

"Occlusion Balloon Catheters: Instructions for Use" Medi-Tech, Boston Scientific Corporation, Rev. Mar. 1991.

Okita et al. "Utilization of Triple–Lumen Balloon Catheter for Occlusion of the Ascending Aorta During Distal Aortic Arch Surgery with Hypothermic Retrograde Cerebral Circulation Technique Through Left Thoracotomy." J Card Surg., 10:699–702 (1995).

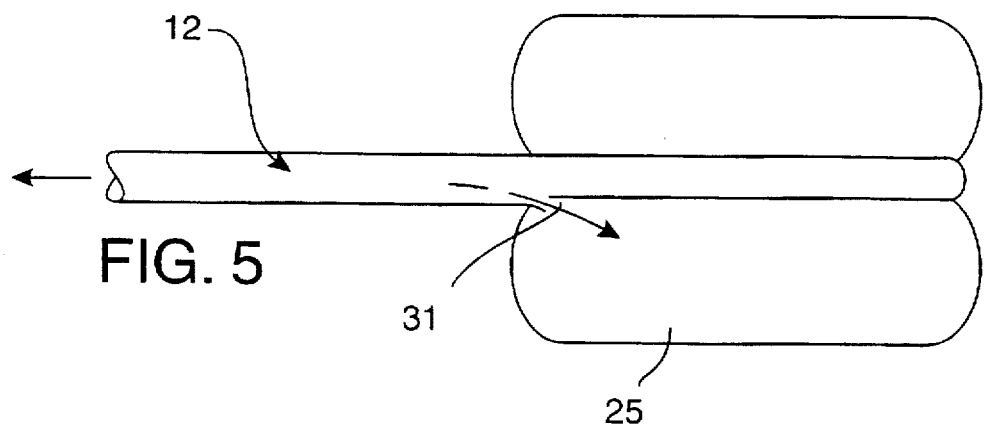
FIG. 5
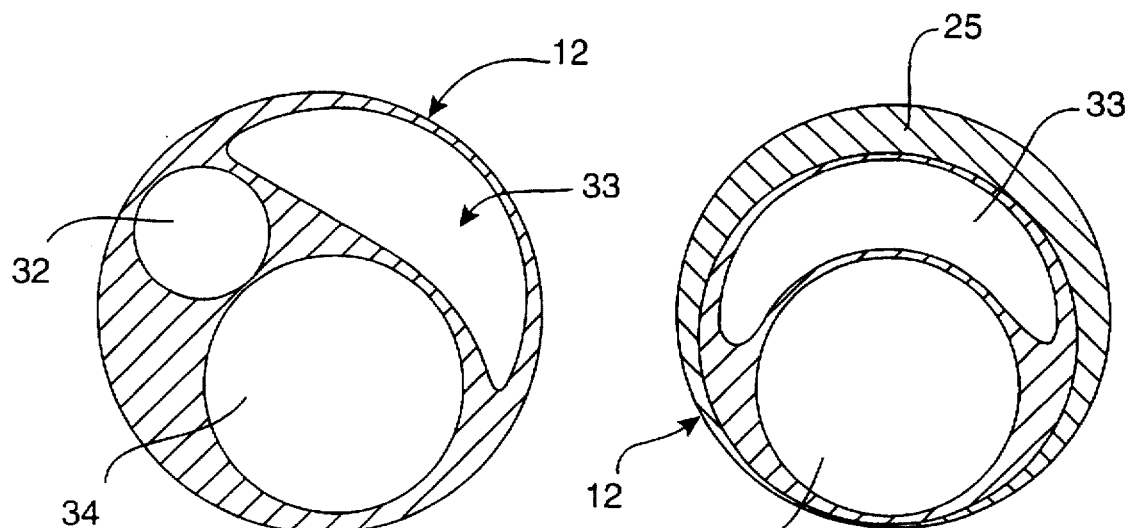
FIG. 6a
FIG. 7
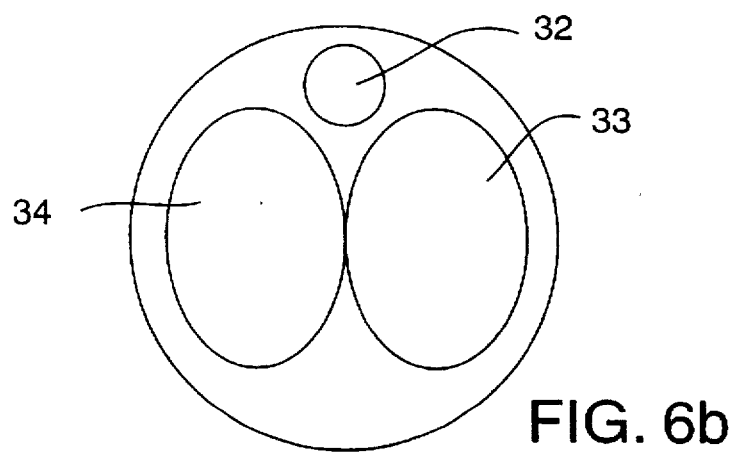
FIG. 6b

1

VENOUS CANNULA

This is a continuation of Ser. No. 08/614,634, filed Mar. 13, 1996, now abandoned, which is a division of Ser. No. 08/427,384, filed Apr. 24, 1995, now U.S. Pat. No. 5,725,496 which is a divisional of application Ser. No. 08/159,815, filed Nov. 30, 1993, which issued on Jul. 18, 1995 as U.S. Pat. No. 5,433,700.

FIELD OF THE INVENTION

The present invention relates to a method for inducing cardioplegic arrest in a heart and to catheters for use in that method.

BACKGROUND OF ART

The use of extracorporeal cardiopulmonary by-pass for cardiac support has become well established. This use has, however, involved median sternotomy or less commonly thoracotomy with all of the trauma that necessarily accompanies such a major surgical procedure.

The present invention contemplates, at least in its preferred embodiments, the possibility of effective ascending aortic occlusion, cardioplegia, venting, right heart deflation and topical cooling in association with extracorporeal cardiopulmonary by-pass all without necessitating a median sternotomy or other thoracic incision.

DISCLOSURE OF THE INVENTION

In a first aspect the present invention consists in a method for inducing cardioplegic arrest of a heart in situ in a patient's body, comprising the steps of:

(a) maintaining systemic circulation with peripheral cardiopulmonary by-pass;

(b) occluding the ascending aorta through a percutaneously placed arterial balloon catheter;

(c) introducing a cardioplegic agent into the coronary circulation; and (d) venting the left side of the heart.

The method according to the present invention may be carried out on humans or other mammalian animals. The method is of particular applicability in humans as it allows an alternative approach to open heart surgery and the development of closed cardioscopic surgery. The method according to the invention enables a percutaneous by-pass system to be associated with cardioplegia, venting and cooling of the heart which subverts the need for median sternotomy. This may, in turn, reduce the complications of the surgery.

The maintenance of the systemic circulation involves establishing a cardiopulmonary by-pass. The blood may be drawn into the by-pass merely by positioning a percutaneous catheter into the right atrium and/or into one or both of the vena cavae through which venous blood may be drawn from the heart into an extracorporeal pump oxygenator. In more preferred embodiments of the invention a single catheter with two inflatable cuffs, or two separate catheters, each with an inflatable cuff are introduced into the vena cavae to occlude them adjacent to their right atrial inlets. This allows isolation of the right atrium and allows blood to be drawn from the vena cavae into the by-pass system. There is also preferably provision for percutaneous communication via one catheter with the right atrium to allow infusion of saline into the right atrium. This infusion has the advantage that it allows the heart to be cooled and improves visual acuity within the right heart allowing direct cardioscopic examination and/or intervention.

The catheter used to decompress the right atrium and to draw blood into the by-pass is preferably introduced through the femoral vein by percutaneous puncture or direct cut down. If other than simple venous drainage is required catheters with inflatable cuffs, as described above, are placed preferably such that an inflatable cuff of the cannula is positioned within each of the inferior (suprahepatic) and superior vena cavae. There is preferably a lumen in the cannula acting as a common blood outlet from the vena cavae leading to the pump oxygenator. A separate lumen is preferably used to infuse saline between the two inflated cuffs into the right atrium. If, alternatively, separate catheters are used to occlude each of the inferior and superior vena cavae then the cannula for the inferior vena cavae is preferably introduced percutaneously from the femoral vein and that for the superior vena cavae is introduced percutaneously through the jugular or subclavian vein.

The ascending aorta is preferably occluded by a balloon catheter introduced percutaneously through the femoral artery. This catheter must carry adjacent its tip an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon is of a cylindrical shape to fully and evenly accommodate the lumen of the ascending aorta. This maximizes the surface area contact with the aorta, and allows for even distribution of occlusive pressure.

The balloon of the catheter is preferably inflated with a saline solution to avoid the possibility of introducing into the patient an air embolism in the event that the balloon ruptured. The balloon should be inflated to a pressure sufficient to prevent regurgitation of blood into the aortic root and to prevent migration of the balloon into the root whilst not being so high as to cause damage or dilation to the aortic wall. An intermediate pressure of the order of 350 mmHg has been proven effective in trials.

The aortic catheter is preferably introduced under fluoroscopic guidance over a suitable guidewire. Transoesophageal echocardiography can alternatively be used for positioning as has been described with reference to the venous catheter. The catheter may serve a number of separate functions and the number of lumina in the catheter will depend upon how many of those functions the catheter is to serve. The catheter can be used to introduce the cardioplegic agent, normally in solution, into the aortic root via one lumen. The luminal diameter will preferably be such that a flow of the order of 250–500 ml/min of cardioplegic solution can be introduced into the aortic root under positive pressure to perfuse adequately the heart by way of the coronary arteries. The same lumen can, by applying negative pressure to the lumen from an outside source, effectively vent the left heart of blood or other solutions. It may also be desirable to introduce medical instruments and/or a cardioscope into the heart through another lumen in the catheter. The lumen should be of a diameter suitable to pass a fibre-optic light camera of no greater than 3 mm diameter. It is however, preferable that the diameter and cross-sectional design of the internal lumina is such that the external diameter of the catheter in its entirety is small enough to allow its introduction into the adult femoral artery by either percutaneous puncture or direct cut-down.

The oxygenated blood returning to the body from the by-pass system may be conveyed into the aorta from another lumen in the cannula carrying the balloon. In this case the returning blood is preferably discharged from the catheter in the external iliac artery. In another embodiment of the invention, and in order to reduce the diameter of the catheter carrying the balloon, a separate arterial catheter of known type may be used to return blood to the patient from the by-pass system. In this case a short catheter is positioned in the other femoral artery to provide systemic arterial blood from the by-pass system. The control-end of the catheter, i.e., that end that remains outside of the body, should have separate ports of attachment for the lumina. The catheter length should be approximately 900 mm for use in humans.

The cardioplegic agent may be any of the known materials previously known to be useful, or in the future found to be useful, as cardioplegic agents. The agent is preferably infused as a solution into the aortic root through one of the lumina of the aortic catheter.

In another aspect the present invention consists in a catheter for use in occluding the ascending aorta comprising an elongate tube having one or more continuous lumina along its length, an inflatable cuff is disposed about the tube adjacent one end thereof, the cuff being of such a size that upon being inflated it is able to occlude the ascending aorta of a patient.

The catheter and method according to the present invention can be used to induce cardioplegic arrest and may be used in a number of surgical procedures. These include the following:

1. Coronary artery revascularisation such as:
   (a) angioscopic laser introduction or angioscopic balloon angioplasty catheter into the coronary arteries via one lumen of the aortic catheter; or
   (b) thoraco dissection of one or both of the mammary arteries with revascularisation achieved by distal anastomoses of the internal mammary arteries to coronary arteries via a small left anterior thoracotomy.
2. Secundum—type arterial septal defect repair such as by:
   (a) "Closed" cardioscopic closure, or
   (b) Closure as an "open" procedure via a mini-right thoracotomy.
3. Sinus venosus defect repairs similar to 2 above.
4. Infundibular stenosis relief by cardioscopic techniques.
5. Pulmonary valvular stenosis relief by cardioscopic techniques.
6. Mitral valve surgery via a small right thoracotomy
7. Aortic stenosis relief by the introduction of instrumentation via a lumen in the aortic catheter into the aortic root.
8. Left ventricular aneurysm repair via a small left anterior thoracotomy.

BRIEF DESCRIPTION OF THE DRAWINGS

Hereinafter given by way of example are preferred embodiments of the present invention described with reference to the accompanying drawings in which:

FIG. 5 is a partly cut away side elevational view of the balloon end of the catheter of FIG. 4 in an inflated condition;

FIG. 6a is a cross-sectional view of the catheter of FIG. 4 intermediate the control end and the balloon end;

FIG. 6b is an alternative cross-sectional arrangement of the lumina in the catheter of FIG. 4;

FIG. 7 is a cross-sectional view through the balloon end of the catheter of FIG. 4;

BEST METHOD OF CARRYING OUT THE INVENTION

Figure 1:
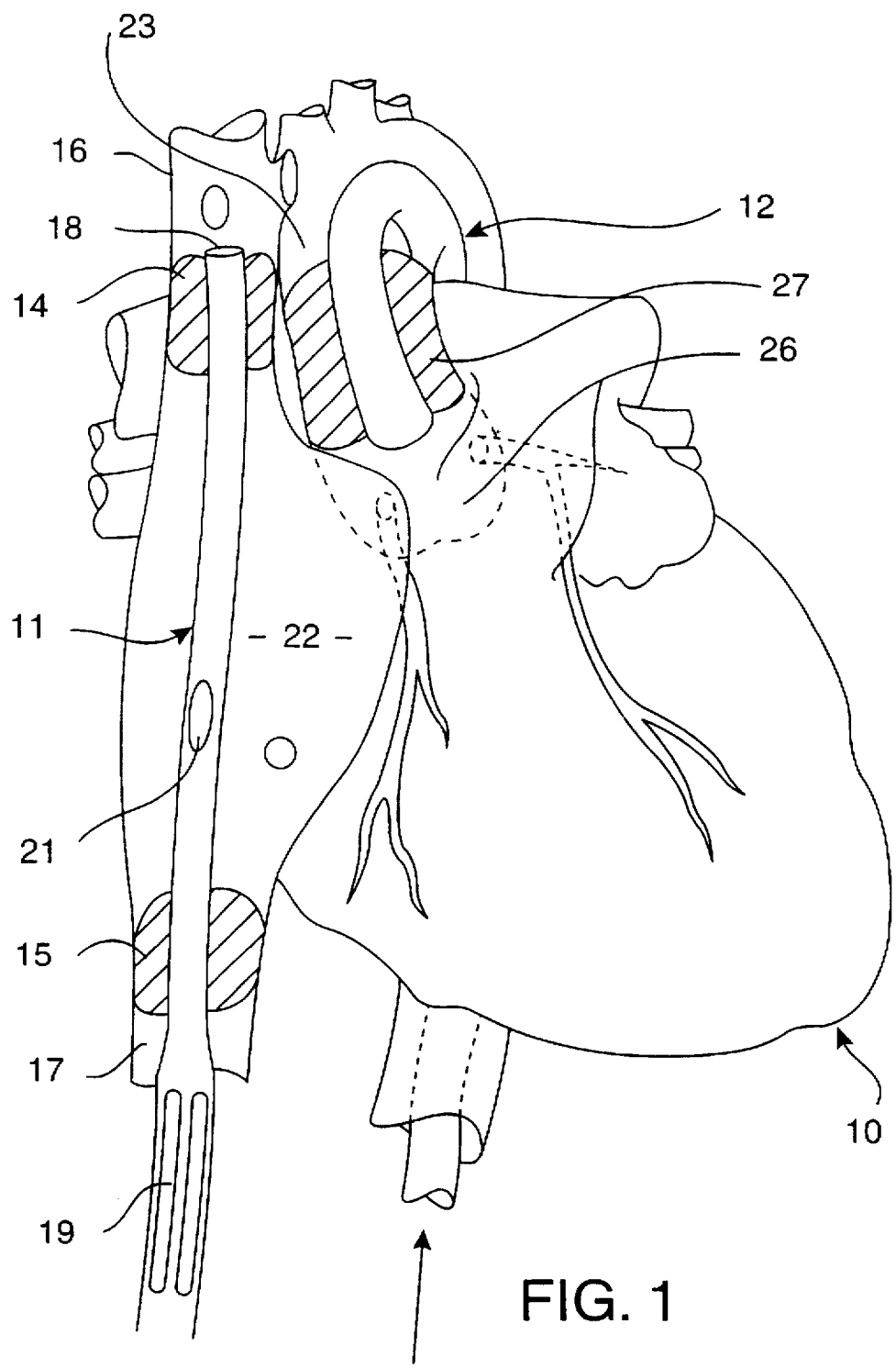
FIG. 1 is a schematic partly cut-away representation of a patients heart having percutaneous catheters placed therein for carrying out the method according to the present invention.
Figure 2:
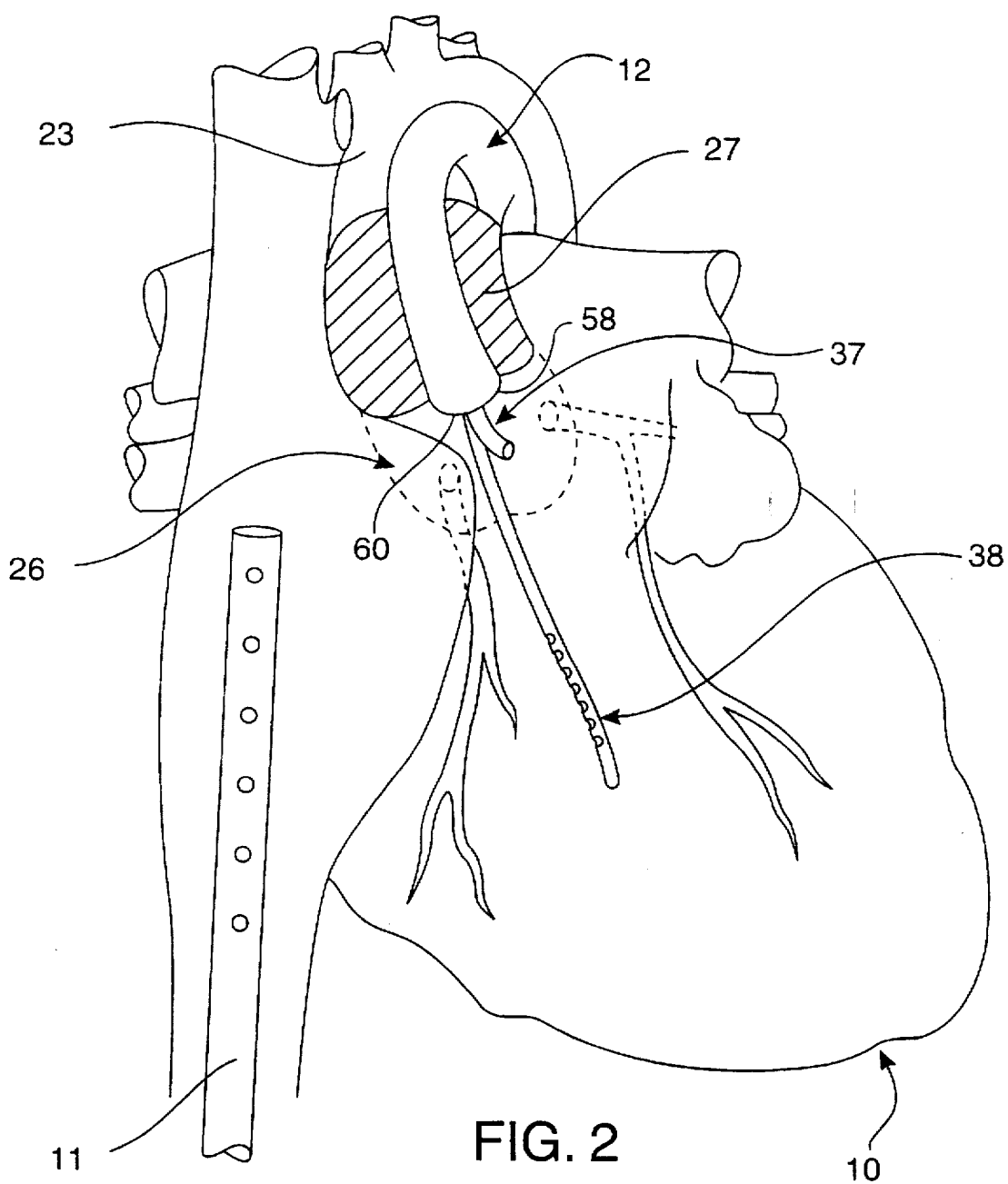
FIG. 2 is a similar view to FIG. 1 showing the aortic catheter in position but including an angioscope and a left ventricular venting cannula introduced into the aortic root and left ventricle respectively, via separate lumina within the aortic catheter.

The heart 10 of FIGS. 1 and 2 is positioned in the living body of a patient and is accessed percutaneously.

In order to induce cardioplegia in the heart while maintaining the patient it is necessary to divert the patients blood circulation through an extracorporeal cardiopulmonary by-pass system 8. This is achieved by isolating the heart 10 on both the venous and arterial sides using appropriate percutaneously inserted venous catheter 11, aortic balloon catheter 12, and if this catheter 12 doesn't have provision for arterial blood return, arterial catheter 39 (see FIG. 3). The venous outflow and arterial inflow lumina of the catheters 11 and 12 of the by-pass system 8 are of sufficient cross sectional area to achieve standard blood flows to maintain the patient's systemic circulation during the period of extracorporeal circulation.

In the case of the use of a single venous double-ballooned catheter 11, as is shown in FIG. 1, the catheter 11 is inserted through the femoral vein preferably. A suitable guide wire is initially inserted and the catheter 11 is then introduced in known manner under fluoroscopic guidance. The catheter 11 includes a pair of separately inflatable balloons 14 and 15 each connected to a balloon inflation control device (not shown) through suitable lumina in the catheter 11. The balloon 14 is adapted to occlude the superior vena cavae 16 while the balloon 15 is adapted to occlude the suprahepatic inferior vena cavae 17. A blood withdrawal lumen in the catheter 11 has an inlet orifice 18 flush with the balloon 14, to avoid venous collapse during blood flow into the catheter 11, and a series of inlet slots 19 in the inferior vena cavae. Blood drawn into the inlets 18 and 19 enter a common single lumen. Blood drawn into the by-pass system through the catheter 11 is oxygenated and returned to the patient in a manner which will be hereinafter described.

A separate lumen in the catheter 11 opens into the right atrium 22 through aperture 21 to allow evacuation of blood from the right heart and the infusion of saline to induce topical cooling and/or to improve visual acuity within the right heart.

Figure 9B:
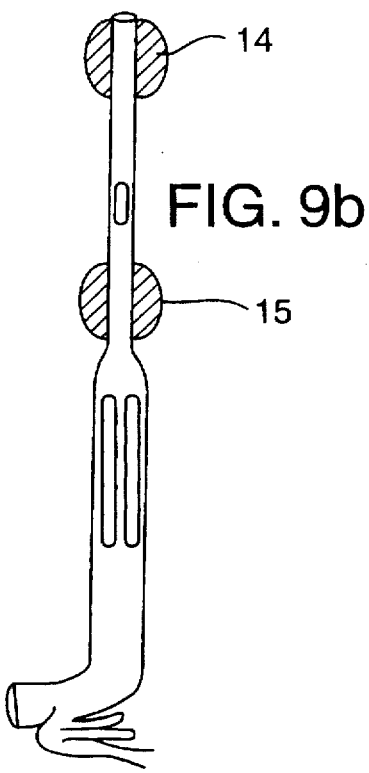
FIGS. 9a and 9b show schematically two alternative catheter arrangements for the isolation of the right atrium and venous drainage.
Figure 9A:
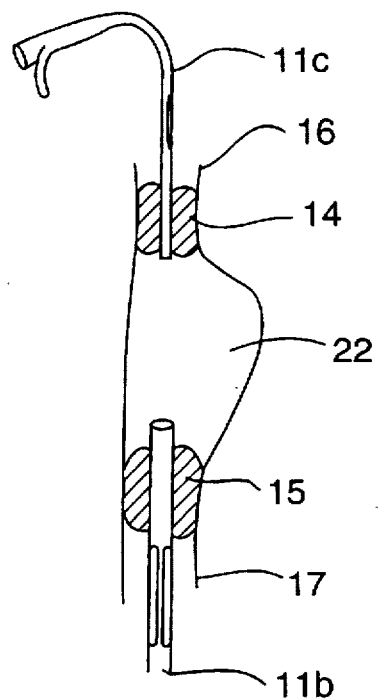

In use, after the catheter 11 has been positioned the balloons may be inflated or deflated to vary the rate of venous return to the right atrium 22 and therefore the degree of decompression of the left heart. Venous drainage may be effected by gravitational drainage or by applying a degree of negative pressure to assist flow into the pump oxygenator. It will be appreciated that the distance between the balloons 14 and 15 will need to be correct for a given patient and this may be assessed by X-ray examination to allow selection of an appropriately sized catheter. Alternatively separate catheters 11b and 11c could be used, as is shown in FIG. 9a, for the inferior and superior vena cavae. The cannula 11b being introduced as has been described above and the cannula 11c being introduced through the jugular or subclavian vein. It will also be appreciated that for simple operations not requiring complete occlusion of the right atrium it is possible to merely insert a simple catheter 11 into the right atrium to draw blood into the by-pass system as is seen in FIG. 2. Positioning under fluoroscopic guidance is not essential in this case.

Figure 3:
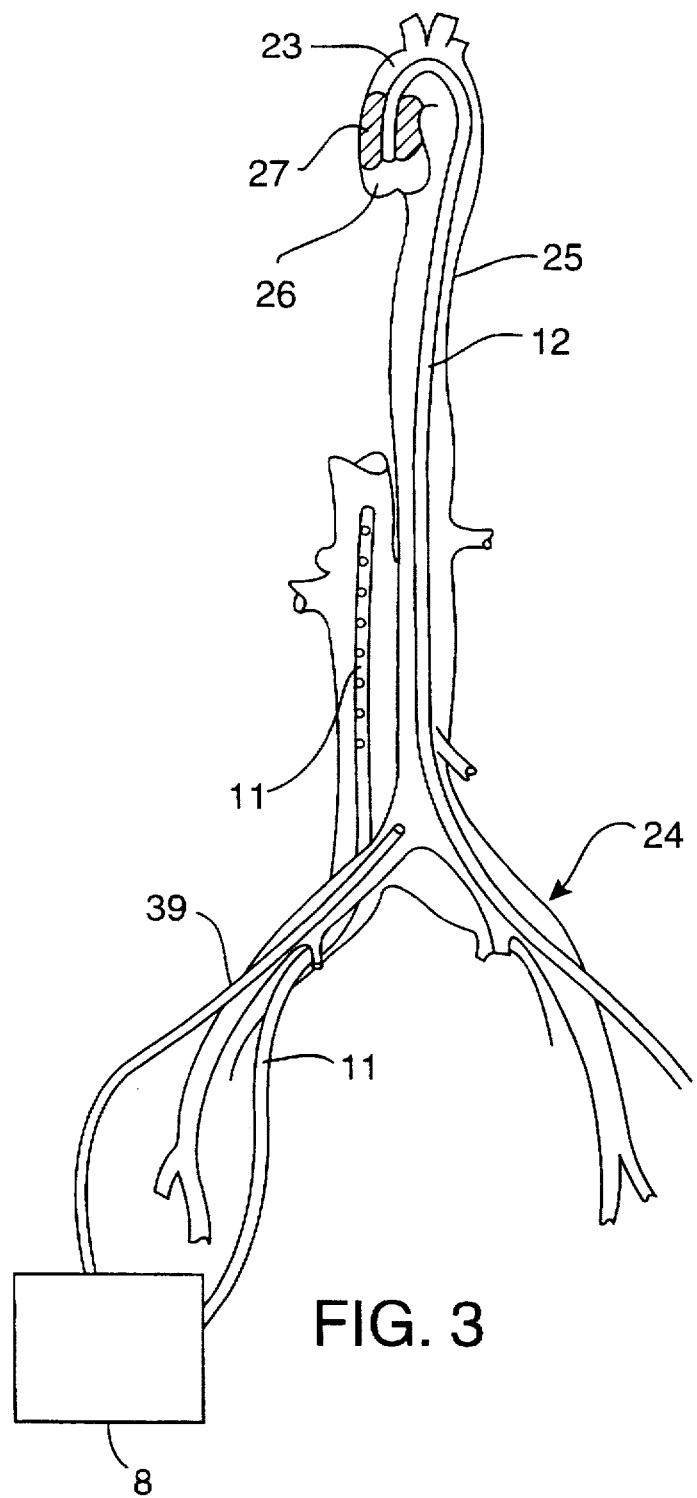
FIG. 3 is a front elevational view of part of the vascular system of a patient showing, inter alia, the aortic balloon catheter positioned in the ascending aorta via the femoral artery.
Figure 4:
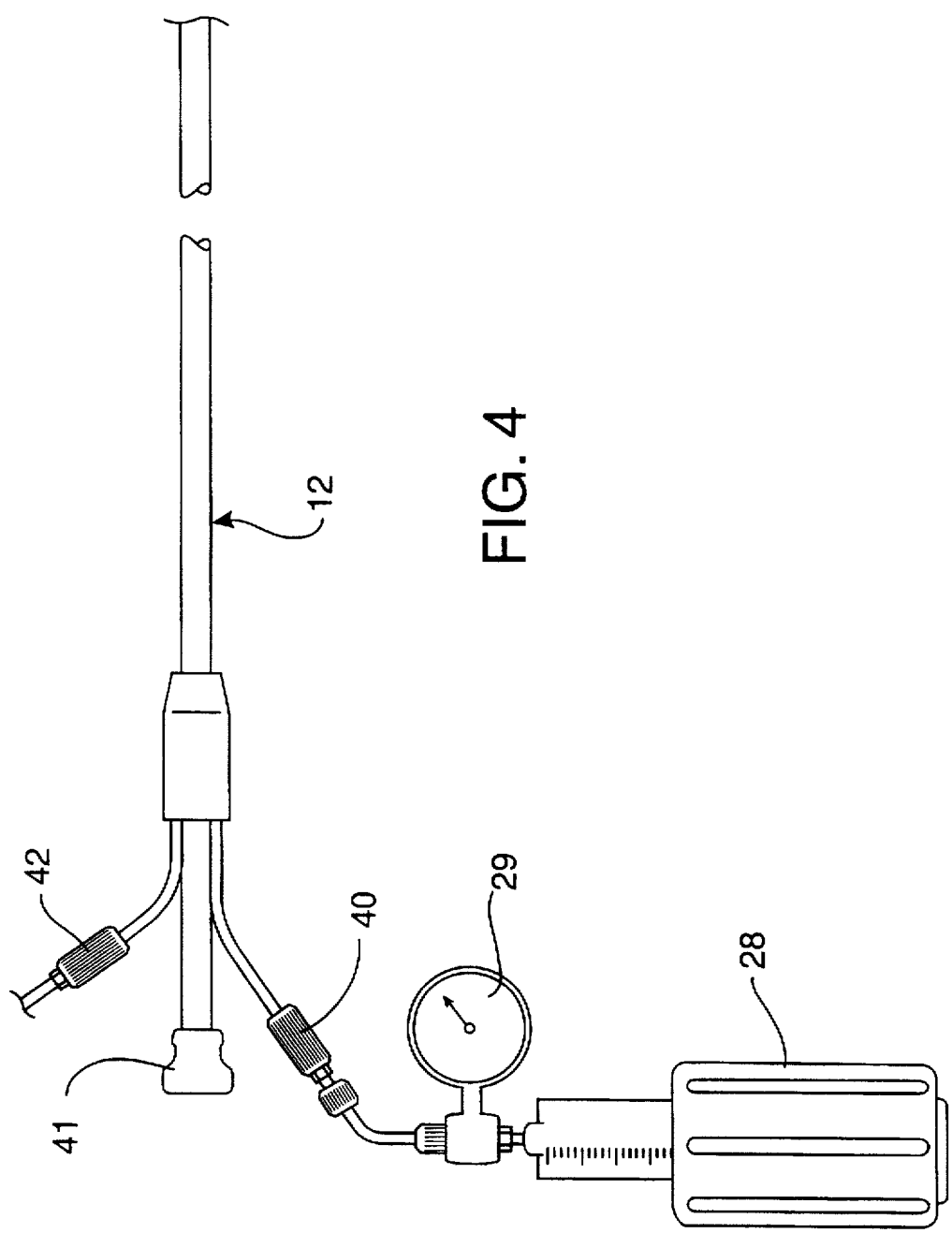
FIG. 4 is a side elevational view of the control end of the aortic catheter according to the present invention.

The catheter 12 is positioned in the manner described above-with its free end located in the ascending aorta 23. The catheter 12 is so positioned by insertion preferably through the femoral artery 24 and via the descending aorta 25 as is seen in FIG. 3.

If desired a fluoroscopic dye may be introduced into the aortic root 26 through the catheter 12 for accurate positioning of the tip of the catheter 12 relative to the aortic root 26 and the coronary ostia.

The catheter 12 carries at its free end a balloon 27. The balloon 27 is arranged to be inflated with saline from an inflation control device 28 of known type through a lumen in the catheter 12. The device 28 is fitted with a pressure gauge 29 to allow the operator to control the inflation of the balloon 27. The pressure of the fully inflated balloon 27 should be of the order of 350 mmHg so as to be sufficient to effectively occlude the aorta and to prevent the balloon moving while not being so great as to cause damage to the aortic wall. The balloon 27 should have a maximum diameter sufficient to occlude the aorta and for this purpose the maximum diameter should be about 35 mm. The balloon 27 should have a length of about 40 mm so as not to be so long as to occlude or impede blood flow to the coronary arteries on to the brachiocephalic, subclavian or carotid arteries. If necessary in any given patient the required length and diameter of the balloon may be determined by angiographic, X-ray examination or echocardiography and an appropriately sized catheter selected on that basis.

The balloon 27 is preferably connected to the lumen 32 through which it is inflated at the end of the balloon 27 distal to the tip of the catheter 12 through orifice 31 (see FIG. 5). This allows the tip of the catheter to contain fewer lumina than the remainder of the catheter. Accommodation of the deflated balloon around the tip of the catheter is thus possible without adding to the diameter of the tip as compared with the rest of the catheter 12.

Figure 8A:
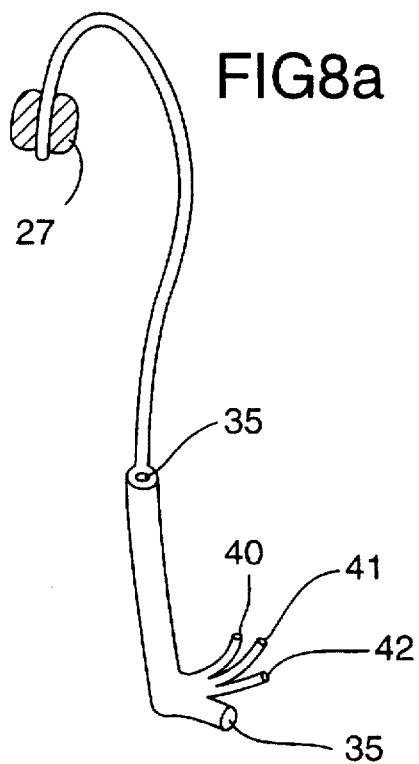
FIGS. 8a and 8b show schematically two alternative arrangements to the catheter shown in FIG. 4.
Figure 8B:
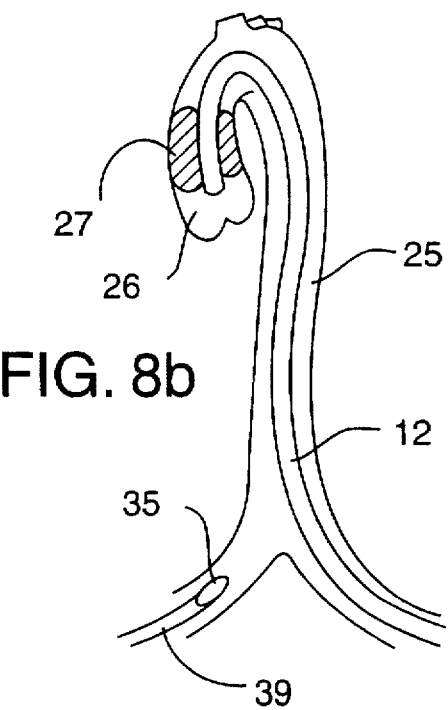

The catheter 12 includes a plurality of lumina (see FIGS. 6 and 7). In addition to the balloon inflation lumen 32 there is at least a single venting/cardioplegia lumen 33 of circular cross-section. There may be a separate and extra circular lumen 34 for instrumentation. If two lumens are present the venting/cardioplegia' lumen may be circular or crescent shaped in cross-section (FIG. 6a, 6b). The diameter of the various lumina should be as small as practicable commensurate with the intended use. In addition there may be a continuous lumen 35 through which arterial blood is returned from the-by-pass. This may flow out of the catheter 12 through an orifice in the region of the external iliac artery. In alternative embodiments of the invention such as shown in FIGS. 3 and 8 the arterial return lumen 35 may comprise its own catheter 39 of known type introduced into the other femoral artery or some other suitable artery.

In use the catheter 12 is introduced percutaneously by puncture or cutdown as has been described and once blood flow through the by-pass is established (including systemic cooling) flows are reduced and the balloon 25 is inflated. Flows are then returned to the operating levels and a suitable cardioplegic agent is introduced into the aortic root. Once the full volume of cardioplegic agent has been given and cardiac arrest achieved, the lumen is then used to vent the heart. The heart may then be operated on or examined by insertion of instrumentation 37 such as a cardioscope or a laser into the heart through the lumen 34 or through atrial trocars. Alternatively, with the heart on by-pass as described above the heart can be approached by an open method by an incision other than median sternotomy. Venting of the left ventricle may be effected by providing an extended cannula 38 projecting from lumen 33 into the left ventricle (see FIG. 2) or by simply applying negative pressure to the venting lumen 33 of the aortic catheter. To reverse cardioplegic arrest the body is rewarmed and the balloon 27 deflated. Aortic blood is thus allowed to perfuse the heart. Whilst the body remains supported by peripheral cardiopulmonary by-pass, the return of the heart rhythm is awaited. External defibrillation may be necessary. Weaning from by-pass is then completed in a routine fashion.

I claim:

1. A system for removing blood from a venous system of a patient and returning oxygenated blood to the patient from an extracorporeal bypass system, the system comprising:

a venous cannula including a shaft having a proximal end, a distal end, a blood withdrawal lumen, and a first inlet in fluid communication with the blood withdrawal lumen for withdrawing blood from a patient, the blood withdrawal lumen being of sufficient size to provide full bypass, the shaft having a length selected so as to extend into at least one of a superior vena cava and an inferior vena cava of the patient from a peripheral vein;

means for occluding a vessel selected from the superior vena cava and the inferior vena cava of the patient, the vessel occluding means being mounted to the shaft and being movable between an expanded shape and a collapsed shape;

an arterial cannula having a blood return lumen, the arterial cannula being configured to be positioned in the patient's vascular system for returning oxygenated blood to the patient; and an extracorporeal bypass system configured to maintain circulation of oxygenated blood in the patient when the patient's heart is arrested;

wherein the blood withdrawal lumen and blood return lumen are both coupled to the bypass system.

2. The system of claim 1, further comprising:

means for occluding an other vessel of the superior vena cava and the inferior vena cava, the other vessel occluding means being mounted to the shaft and being movable between a collapsed shape and an expanded shape.

3. The system of claim 2 wherein:

the shaft includes a fluid port and a second lumen, the fluid port being fluidly coupled to the second lumen and being disposed between the vessel and other vessel occluding means.

4. The system of claim 2, wherein:

the shaft includes a second inlet positioned distal of the other vessel occluding means.

5. The system of claim 4, wherein:

the second inlet is fluidly coupled to the blood withdrawal lumen.

6. A system for removing blood from a venous system of a patient and returning oxygenated blood to the patient from an extracorporeal bypass system, the system comprising:

a first venous cannula having a first shaft and means for occluding a patient's superior vena cava, the first shaft having a proximal end, a distal end, and a first blood withdrawal lumen, the first shaft having a length selected so as to extend into the superior vena cava of the patient from a peripheral vein, the superior vena cava occluding means being mounted to the first shaft and movable between an expanded shape and a collapsed shape;

a second venous cannula having a second shaft and means for occluding the inferior vena cava, the second shaft having a proximal end, a distal end, and a second blood withdrawal lumen, the second shaft having a length selected so as to extend into the inferior vena of the patient from a peripheral vein, the inferior vena cava occluding means being mounted to the second shaft and movable between an expanded shape and a collapsed shape; and an extracorporeal bypass system configured to maintain circulation of oxygenated blood in the patient when the patient's heart is arrested;

the first and second blood withdrawal lumens being coupled to the bypass system.

* * * * *